US010429353B2

(12) United States Patent
Murayama

(10) Patent No.: US 10,429,353 B2
(45) Date of Patent: Oct. 1, 2019

(54) PHOTOACOUSTIC MICROSCOPE AND PHOTOACOUSTIC SIGNAL DETECTION METHOD

(71) Applicant: OLYMPUS CORPORATION, Tokyo (JP)

(72) Inventor: Yoshiaki Murayama, Machida (JP)

(73) Assignee: Olympus Corporation, Tokyo (JP)

( * ) Notice: Subject to any disclaimer, the term of this patent is extended or adjusted under 35 U.S.C. 154(b) by 205 days.

(21) Appl. No.: 15/603,857

(22) Filed: May 24, 2017

(65) Prior Publication Data

US 2017/0254784 A1    Sep. 7, 2017

Related U.S. Application Data

(63) Continuation of application No. PCT/JP2014/081502, filed on Nov. 28, 2014.

(51) Int. Cl.
| | |
|---|---|
| *G01N 29/24* | (2006.01) |
| *G02B 21/00* | (2006.01) |
| *G02B 21/36* | (2006.01) |
| *G01N 29/44* | (2006.01) |

(Continued)

(52) U.S. Cl.
CPC ..... *G01N 29/2418* (2013.01); *G01N 21/1702* (2013.01); *G01N 29/0681* (2013.01);
(Continued)

(58) Field of Classification Search
CPC ..... G01N 21/1702; G01N 2291/02466; G01N 2291/26; G01N 29/0681; G01N 29/11;
(Continued)

(56) References Cited

U.S. PATENT DOCUMENTS

| | | | |
|---|---|---|---|
| 6,108,096 A | * | 8/2000 | Ushio ................ G01N 21/1702 356/432 |
| 9,084,560 B2 | | 7/2015 | Sato et al. |

(Continued)

FOREIGN PATENT DOCUMENTS

| | | |
|---|---|---|
| JP | 2002-257793 A | 9/2002 |
| JP | 2003-130852 A | 5/2003 |

(Continued)

OTHER PUBLICATIONS

English translation of International Preliminary Report on Patentability dated Jun. 8, 2017 together with the Written Opinion received in related International Application No. PCT/JP2014/081502.

(Continued)

*Primary Examiner* — John H Le
(74) *Attorney, Agent, or Firm* — Scully Scott Murphy & Presser, P.C.

(57) ABSTRACT

A photoacoustic microscope includes: a light source which generates pulse light; a focusing optical system which focuses the pulse light emitted from the light source and irradiate a sample with the focused pulse light; a photoacoustic signal detection unit which detects an acoustic signal generated from the sample through irradiation of the pulse light; an image signal formation unit which forms an image signal of the sample based on the acoustic signal; an information unit having information representing a relation between intensity of the pulse light entering the sample and intensity of the acoustic signal generated from the sample; and a pulse light intensity changing unit which changes intensity of the pulse light from the light source based on the information.

14 Claims, 9 Drawing Sheets

(51) Int. Cl.
*G02B 21/06* (2006.01)
*G01N 29/06* (2006.01)
*G01N 29/11* (2006.01)
*G01N 29/48* (2006.01)
*G01N 21/17* (2006.01)

(52) U.S. Cl.
CPC ............. *G01N 29/11* (2013.01); *G01N 29/44* (2013.01); *G01N 29/48* (2013.01); *G02B 21/0036* (2013.01); *G02B 21/06* (2013.01); *G02B 21/368* (2013.01); *G01N 2291/02466* (2013.01); *G01N 2291/26* (2013.01)

(58) Field of Classification Search
CPC .... G01N 29/2418; G01N 29/44; G01N 29/48; G02B 21/0036; G02B 21/06; G02B 21/368
USPC ....... 702/56, 104; 382/128; 73/655; 600/431
See application file for complete search history.

(56) References Cited

U.S. PATENT DOCUMENTS

| | | |
|---|---|---|
| 9,226,662 B2 | 1/2016 | Someda |
| 9,392,944 B2* | 7/2016 | Kasamatsu .......... A61B 5/0095 |
| 2011/0106478 A1 | 5/2011 | Someda |
| 2013/0031982 A1 | 2/2013 | Sato et al. |
| 2014/0005537 A1* | 1/2014 | Asami ................. A61B 5/0095 |
| | | 600/431 |
| 2014/0286549 A1 | 9/2014 | Fukutani |

FOREIGN PATENT DOCUMENTS

| | | |
|---|---|---|
| JP | 2011-120795 A | 6/2011 |
| JP | 2014-180492 A | 9/2014 |
| WO | WO 2011/052061 A1 | 5/2011 |

OTHER PUBLICATIONS

Yao, J. et al., "Photoimprint Photoacoustic Microscopy for Three-Dimensional Label-Free Subdiffraction Imaging" Physical Review Letters, American Physical Society, PRL 112, 014302 (2014), Jan. 10, 2014, pp. 014302-1-014302-5.

Japanese Office Action dated Aug. 8, 2018 in Japanese Patent Application No. 2016-561181.

International Search Report dated Feb. 10, 2015, issued in PCT/JP2014/081502.

* cited by examiner

PHOTOACOUSTIC MICROSCOPE AND PHOTOACOUSTIC SIGNAL DETECTION METHOD

CROSS-REFERENCE TO RELATED APPLICATION

The present application is a continuation of PCT/JP2014/081502, filed on Nov. 28, 2014, which claims priority to PCT/2014/081502; the entire contents of which are incorporated herein by reference.

BACKGROUND OF THE INVENTION

Field of the Invention

The present invention relates to a photoacoustic microscope and a photoacoustic signal detection method.

Description of the Related Art

Photoacoustic waves are one kind of elastic waves generated in the process of thermoelastic phenomenon caused when a substance is irradiated with light having an absorption wavelength band. Photoacoustic imaging is thus drawing attention as a method for imaging absorption characteristics.

A photoacoustic microscope, which applies photoacoustic waves to a detection signal for imaging, employs a method involving using pulse light adjusted to an absorption wavelength band of an object to be observed as excitation light, focusing the excitation light by an objective lens to scan the inside of a sample with a focused spot, and detecting photoacoustic waves generated at each focused spot position by a transducer or other such devices.

An example of the configuration of the photoacoustic microscope configured to acquire a super-resolved image is proposed in J. Yao, L. Wang, C. Li, C. Zhang, and L. V. Wang, "Photoimprint Photoacoustic Microscopy for Three-Dimensional Label-Free Subdiffraction Imaging," Physical Review Letters 112(1), 014302 (January 2014). The proposed photoacoustic microscope photographs the same place twice. A sample is first photographed such that an area around the center of an optical spot is bleached more than the vicinity of the optical spot. Measuring the same place once again and determining a signal difference enables the diameter of the spot bleached by the first photographing to be acquired. As a result, a super-resolved image can be acquired.

SUMMARY OF THE INVENTION

A photoacoustic microscope according to the present invention includes:

a light source which generates pulse light;

a focusing optical system which focuses pulse light generated from the light source and irradiating a sample with the focused pulse light;

a photoacoustic signal detection unit which detects an acoustic signal generated from the sample through irradiation of the pulse light;

an image signal formation unit which forms an image signal of the sample on the basis of the acoustic signal;

an information unit having information representing a relation between intensity of the pulse light entering the sample and intensity of the acoustic signal generated from the sample; and a pulse light intensity changing unit which changes intensity of the pulse light from a light source on the basis of the information.

A photoacoustic signal detection method according to another aspect of the present invention includes:

emitting pulse light;

focusing the pulse light emitted at the emission step and irradiating a sample with the focused pulse light;

detecting an acoustic signal generated from the sample through irradiation of the pulse light;

forming an image signal of the sample based on the acoustic signal;

providing an information representing a relation between intensity of the pulse light entering the sample and intensity of the acoustic signal generated from the sample; and changing intensity of the pulse light from a light source based on the information.

DETAILED DESCRIPTION OF THE INVENTION

Functions and effects obtained by the configuration of a photoacoustic microscope and a photoacoustic signal detection method in embodiments are now described. The present invention is not intended to be limited by the embodiments. Specifically, the description of embodiments includes many specific detailed contents for the illustrative purposes, but various variations and changes of the detailed contents do not depart from the scope of the present invention. Thus, the illustrative embodiments of the present invention are described below without loss of generality or any limitation on the claimed invention.

First Embodiment

First, super-resolution in a photoacoustic microscope according to a first embodiment is described.

Figure 1A:
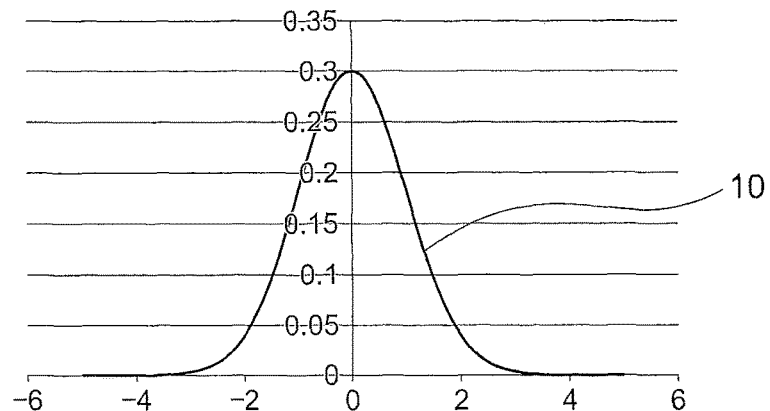
FIGS. 1A to 1D are diagrams illustrating the outline of super-resolution obtained by a photoacoustic signal.

FIG. 1A illustrates an intensity distribution in one line of pulse light that irradiates a sample, which is an object to be observed in the first embodiment, from an objective lens and is focused by the objective lens. The horizontal axis represents positions and the vertical axis represents intensity, each of which has an arbitrary unit. It is assumed that the pulse light is focused to an optical resolution limit.

Figure 1B:
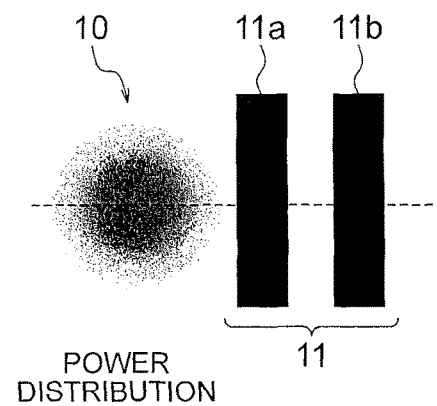
Figure 1C:
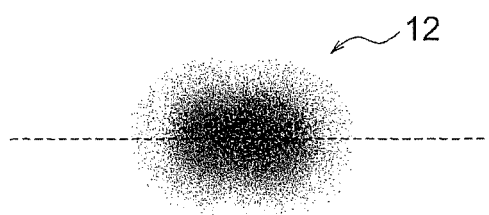

FIG. 1B illustrates the state in which pulse light 10 scans a chart 11 along the direction of the dotted line. The chart 11 has two rectangular charts 11a and 11b arranged side by side with an interval that cannot be resolved by optical observation.

Figure 2A:
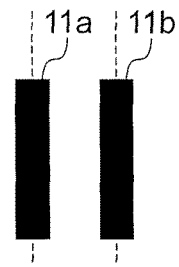
FIGS. 2A to 2F are diagrams illustrating the outline of the super-resolution obtained by the photoacoustic signal.
Figure 2B:
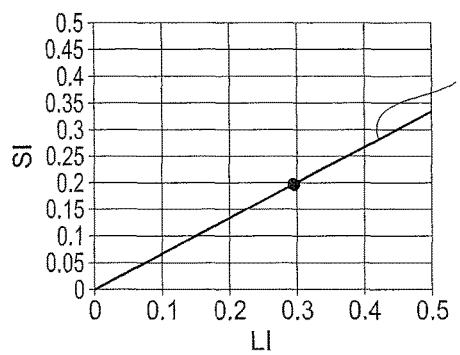

FIG. 2B illustrates a general relation between intensity LI (horizontal axis: arbitrary unit) of incident light to a sample among light beams from a light source and intensity SI (horizontal axis: arbitrary unit) of an observed acoustic signal. In the drawings referred to below, the horizontal axis and the vertical axis have arbitrary units unless otherwise specified. On the scale illustrated in FIG. 2B, the intensity LI of the incident light and the intensity SI of the acoustic signal have a linear relation indicated by a straight line 14.

Figure 2C:
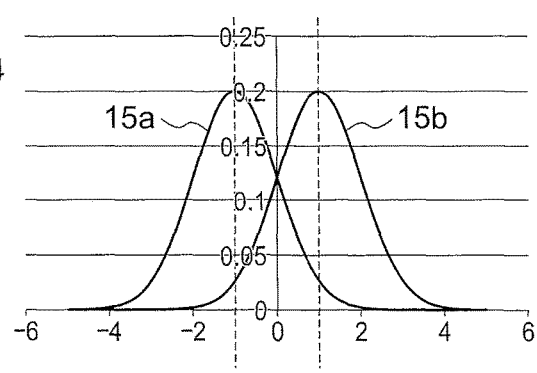

FIG. 2C illustrates intensity distributions 15a and 15b in an optical image obtained by photographing the charts 11a and 11b with photoacoustic waves in the case where the intensity LI of the incident light and the intensity SI of the acoustic signal have the linear relation indicated by the straight line 14. The horizontal axis represents positions, and the vertical axis represents image intensity.

Figure 2D:
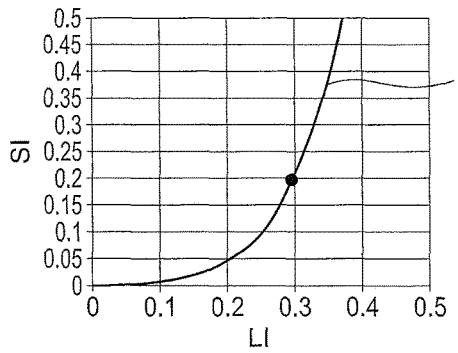
Figure 2E:
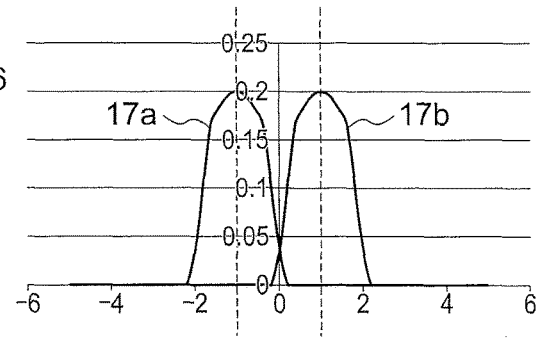
Figure 2F:
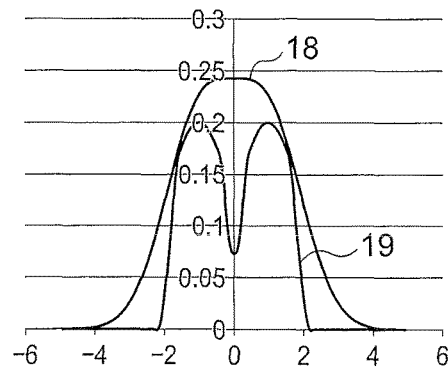

An intensity distribution 18 in FIG. 2F is an intensity distribution obtained by adding the intensity distributions 15a and 15b in the optical image. As is apparent from the intensity distribution 18, it is understood that the charts that cannot be optically resolved cannot be resolved by a conventional photoacoustic microscope.

FIG. 10 illustrates an image 12 observed in this case.

Figure 1D:
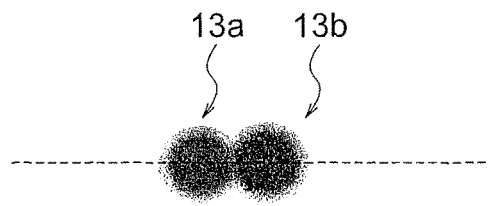

On the other hand, FIG. 2D is a diagram illustrating information (curve 16) representing a relation between intensity (horizontal axis) of pulse light entering a sample and intensity (vertical axis) of an acoustic signal generated from the sample in the first embodiment. In FIG. 2D, for example, an image intensity signal decreases curvilinearly in a region where image intensity is smaller than 0.2. Photographing the charts with the incident intensity LI near an inflection point that appears in the graph of LI and SI, for example, incident intensity of 0.3, enables two photoacoustic signals 17a and 17b illustrated in FIG. 2E to be obtained. FIG. 1D illustrates images 13a and 13b observed in this case.

FIG. 2F illustrates a signal intensity distribution 19 obtained by adding the photoacoustic signals 17a and 17b. As is apparent from the signal intensity distribution 19, it is understood that the charts that cannot be optically resolved can be resolved by the photoacoustic microscope in the first embodiment.

Figure 3A:
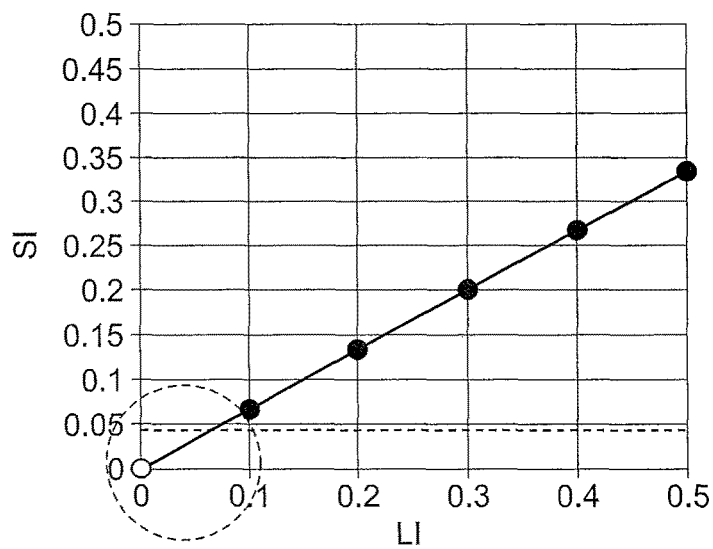
FIGS. 3A and 3B are diagrams illustrating the outline for calculating a threshold.
Figure 3B:
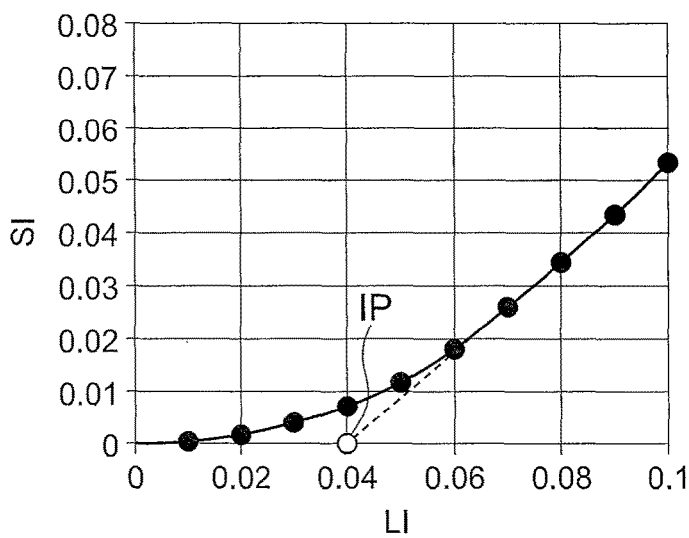

The relation as illustrated in FIG. 2D may be present at a rising of the signal. In many cases, however, the relation as indicated by the curve in FIG. 2D may be generated in a region corresponding to an incident light amount portion smaller than an incident light adjustment minimum unit. For example, the cases in FIGS. 3A and 3B are considered. When a threshold IP is 0.04 and LI is adjusted in units of 0.1, the intensity LI of the incident light and the intensity SI of the acoustic signal have a linear relation as illustrated in FIG. 3A.

When the intensity LI of the incident light is adjusted in units of 0.01, the intensity LI of the incident light and the intensity SI of the acoustic signal have a curvilinear relation as illustrated in FIG. 3B.

FIG. 3B enlarges a portion surrounded by a dotted circle in FIG. 3A. In FIG. 3B, a threshold IP of 0.04 is determined as an intersection between a dotted line extended from a linear part of the curve indicated by the solid line and the intensity SI of 0. When power LI per pulse that irradiates the sample is the threshold IP, a super-resolved image can be obtained as indicated by a signal intensity distribution 19 in FIG. 2F.

Figure 4A:
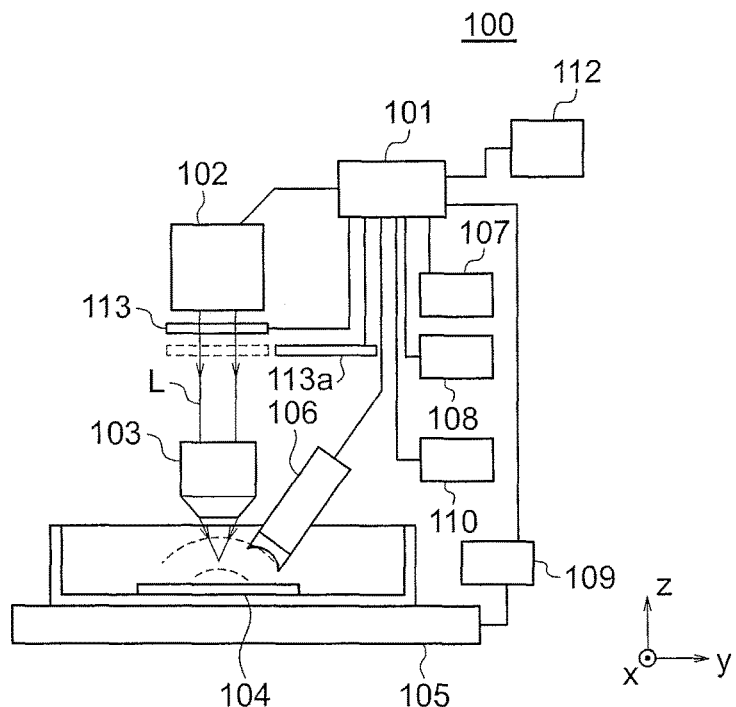
FIG. 4A is a diagram illustrating a schematic configuration of a photoacoustic microscope according to a first embodiment.

FIG. 4A illustrates a schematic configuration of a photoacoustic microscope 100 in the first embodiment. The photoacoustic microscope 100 in the first embodiment is configured to automatically measure a sample. A light source 102 generates pulse light. An objective lens 103, which is a focusing optical system, focuses the pulse light generated from the light source 102 and irradiates a sample 104 with the focused pulse light.

For example, when the sample 104 is a living body and blood vessels in the living body are intended to be imaged, the pulse light source 102 emits excitation light having an absorption wavelength of hemoglobin. The object to be observed is not limited to blood vessels, and the present invention is applicable to imaging of endogenous substances, such as melanin. In this case, light having an absorption wavelength of a substance to be observed is used as pulse light (excitation light) L.

The present invention is also applicable to imaging of exogenous substances, such as phosphor and metal nanoparticles. For phosphor, light having an absorption wavelength band of phosphor to be observed is used as pulse light (excitation light) L. For metal nanoparticles, light having a resonance wavelength band of metal nanoparticles to be observed is used as pulse light (excitation light) L.

When a plurality of absorbing substances are present in the sample 104, it is desired to use light having a peak wavelength of an absorption spectrum characteristic to an object to be observed. Emission timing of the pulse light from the pulse light source 102 is controlled by the control unit 101.

The pulse light L from the pulse light source 102 passes through a variable ND filter 113 to enter the objective lens 103. Examples of the variable ND filter 113 that can be used include a liquid crystal filter capable of changing its transmittance in the range of from 0% to 100%. In order to determine the threshold IP, the amount of light of the pulse light L is adjusted by the variable ND filter 113 in accordance with a flowchart described later.

The pulse light (excitation light) L output from the objective lens 103 focuses on a focus position of the objective lens 103. The sample 104 is disposed so as to overlap with a focused spot of the pulse light (excitation light) L.

A photoacoustic signal detection unit 106 detects an acoustic signal generated from the sample through irradiation of the pulse light. It is desired that a photoacoustic wave transmission medium through which photoacoustic waves easily propagates, such as water, be filled at least between the objective lens 103 and the sample 104 and between the sample 104 and the photoacoustic signal detection unit 106.

The photoacoustic signal detection unit 106 is, for example, a transducer configured to detect photoacoustic waves. The photoacoustic signal detection unit 106 outputs a waveform of photoacoustic waves with respect to a temporal change to an image signal formation unit 110 via a control unit 101 as an output signal. The image signal formation unit 110 forms an image signal of the sample 104 on the basis of the acoustic signal.

The stage drive unit 109 moves the position of the stage 105 two-dimensionally (orthogonal two axes, within xy plane) or three-dimensionally (orthogonal three axes, within xyz plane) relative to the pulse light L and the sample 104. The photoacoustic signal detection unit 106 has an acoustic lens, which has a concave surface facing the sample, at a distal end portion on the sample side. The objective lens 103 and the acoustic lens are desired to maintain a confocal relation. Thus, in the first embodiment, the stage 105 is two-dimensionally or three-dimensionally driven to the confocal position. In this manner, a planar or stereoscopic acoustic signal of the sample 104 can be acquired.

An information generation unit 107 generates information representing a relation between intensity of pulse light entering a sample and intensity of an acoustic signal generated from the sample. The information generation unit 107 corresponds to an information unit.

Light output from the pulse light source 102 passes through the variable ND filter 113. The variable ND filter 113 has a function of adjusting the amount of light that irradiates the sample 104.

A threshold calculation unit 112 calculates, on the basis of the information, as a threshold IP, pulse light intensity at which the intensity of the acoustic signal relative to the intensity of the pulse light L starts to increase.

Figure 5:
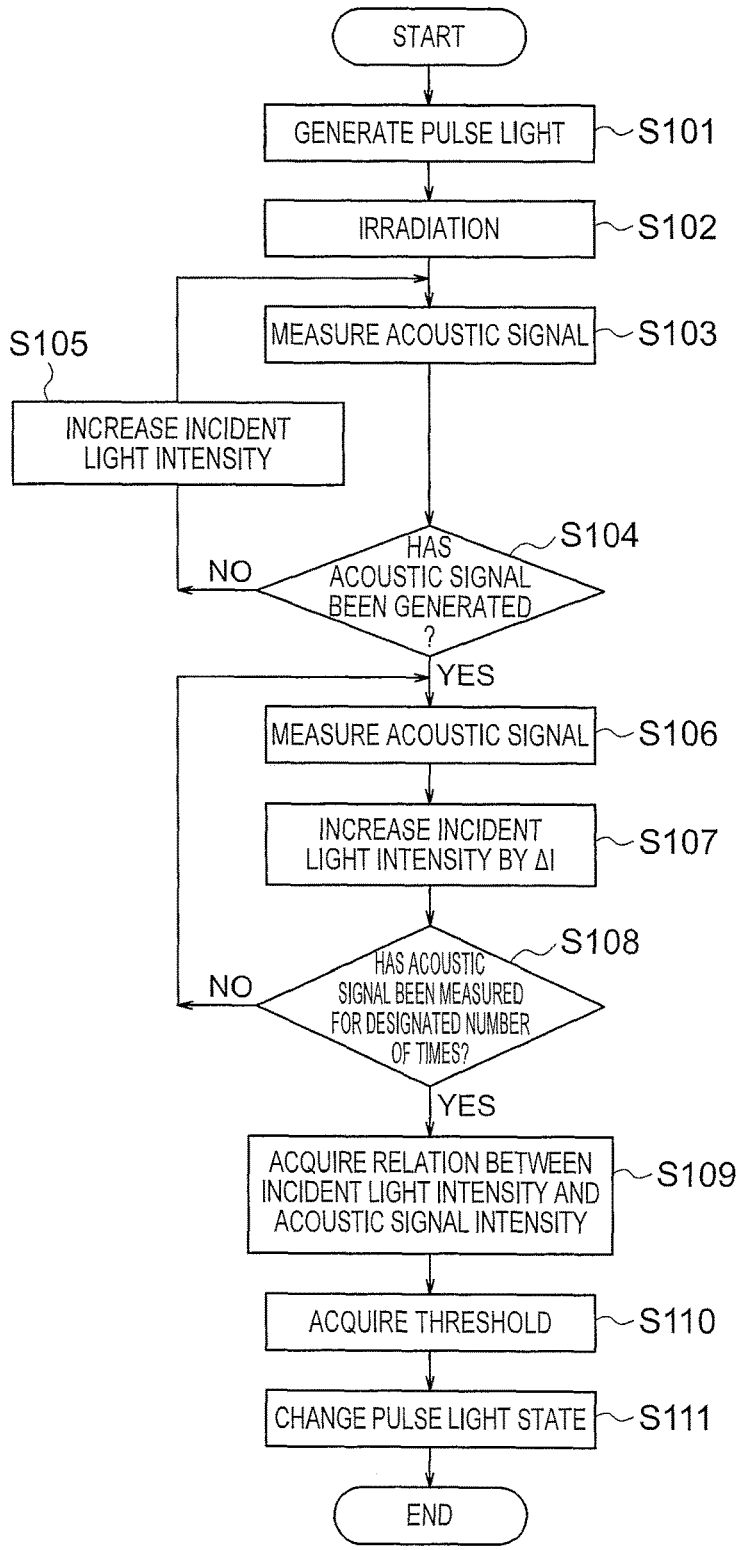
FIG. 5 is a flowchart illustrating a photoacoustic detection method for the photoacoustic microscope according to the first embodiment.

Next, a procedure of a photoacoustic signal detection method in the first embodiment is described with reference to a flowchart of FIG. 5.

First, at Step S101, the pulse light source 102 outputs pulse light L. In this case, the control unit 101 controls the variable ND filter 113 disposed in an optical path such that the transmittance is minimum (that is, the transmitted amount of light is minimum). The pulse light L is focused by the objective lens 103. At Step S102, the sample 104 is irradiated with the focused pulse light L.

At Step S103, the photoacoustic signal detection unit 106 detects an acoustic signal generated from a sample through irradiation of pulse light L. At Step S104, the control unit 101 determines whether the acoustic signal has been generated. When the result of determination at Step S104 is false (No), the flow proceeds to Step S105. At Step S105, the control unit 101 adjusts the transmittance of the variable ND filter 113 to be larger than the current transmittance, that is, increases the amount of light.

When the result of determination at Step S104 is true (Yes), at Step S106, the photoacoustic signal detection unit detects an acoustic signal from the sample 104. At Step S107, the control unit 101 increases the transmittance of the variable ND filter 113 by a predetermined amount. The detection of the acoustic signal is repeated. At Step S108, it is determined whether the acoustic signals have been measured for a designated number of times.

When the result of determination at Step S108 is No, the flow proceeds to Step S106. An acoustic signal is measured in a manner that the amount of incident light to the sample 104, that is, the intensity obtained by changing power per pulse output from the pulse light source 102 by the variable ND filter 113 is changed.

When the result of determination at Step S108 is Yes, the flow proceeds to Step S109. At Step S109, the information generation unit 107 generates information representing a relation between the intensity obtained by changing power per pulse output from the pulse light source 102 by the variable ND filter 113 and the intensity of the acoustic signal generated from the sample 104.

At Step S110, the threshold calculation unit 112 calculates, as the threshold IP, pulse light intensity at which the intensity of the acoustic signal relative to the intensity of the pulse light L starts to increase. At Step S111, the control unit 101 sets the transmittance of the variable ND filter 113 to the transmittance with which the threshold IP is obtained. In this manner, the amount of the pulse light L can be adjusted to obtain a super-resolved image.

Figure 6A:
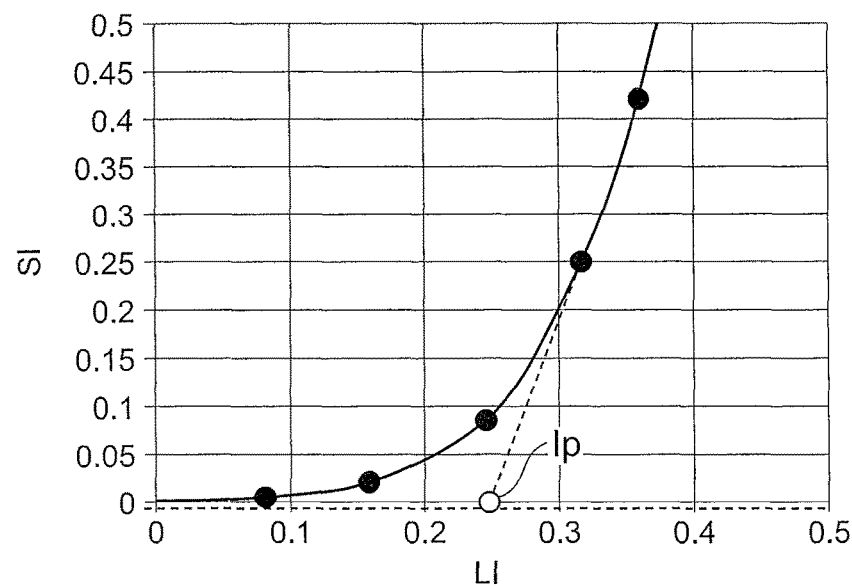
FIGS. 6A and 6B are diagrams for describing the calculation of a threshold and the super-resolution.

FIG. 6A is a diagram illustrating the information and the threshold IP obtained in the first embodiment. Plotting the relation between the intensity LI (horizontal axis) obtained by changing power per pulse output from the pulse light source 102 by the variable ND filter 113 and the intensity S1 (horizontal axis) of the acoustic signal generated from the sample 104 obtains a characteristic curve indicated by the solid line.

In this case, the threshold calculation unit 112 calculates, as a threshold IP, pulse light intensity at which the intensity SI of the acoustic signal relative to the intensity LI obtained by changing power per pulse output from the light source by the variable ND filter starts to increase. Specifically, an intersection between a straight line (indicated by dotted line in FIG. 6A) extended from a linear part of the characteristic curve indicated by the solid line and the intensity SI=0 of the acoustic signal is set as the threshold IP.

In the case where the intensity LI obtained by changing power per pulse output from the light source by the variable ND filter and the intensity SI of the acoustic signal do not have a curvilinear relation, that is, have a linear relation, the threshold IP is present in a region smaller than the minimum adjustment unit of the variable ND filter 113.

In this case, for example, an additional ND filter 113a configured to adjust the amount of light to 1/10 is inserted in the optical path. A threshold IP is determined by the above-mentioned procedure. In FIG. 4A, the additional ND filter 113a is configured to selectively move to the position indicated by the solid line retreated from the optical path and the position indicated by the dotted line inserted in the optical path.

With the additional ND filter 113a inserted in the optical path, a photoacoustic signal is detected in accordance with the procedure described above with reference to FIG. 5. In this manner, the threshold IP can be calculated even when the threshold IP is present in a region smaller than the minimum adjustment unit of the variable ND filter 113.

In the first embodiment, the variable ND filter 113 is desired to change, on the basis of the threshold IP calculated by the threshold calculation unit 112, the intensity of the pulse light from the pulse light source 102 such that the following Conditional Expression (1) is satisfied:

$$1.05 < IP/IT < 2.7 \tag{1}$$

where IT is the threshold calculated by the threshold calculation unit 112, and IP is a peak value of intensity at a focus position of the pulse light after the change.

Conditional Expression (1) defines the condition that an appropriate super-resolved image is obtained. When IP/IT falls below the lower limit value in Conditional Expression (1), no pulse light comes from the light source. When IP/IT exceeds the upper limit value in Conditional Expression (1), the resolution necessary for super-resolution cannot be obtained.

Figure 6B:
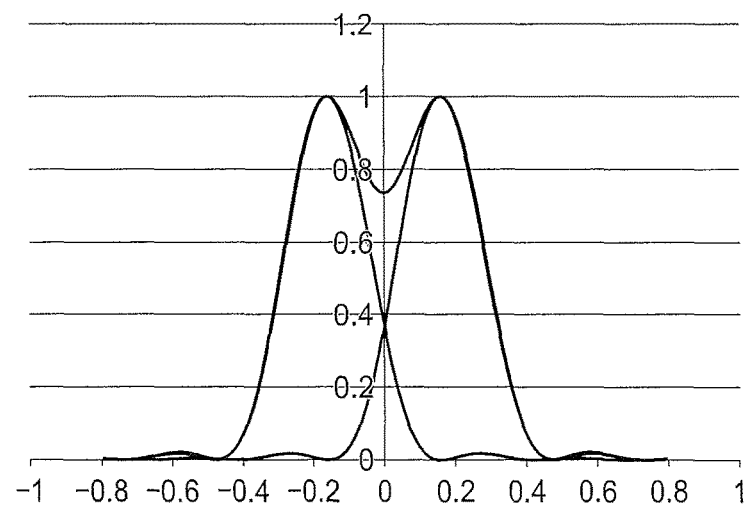

Increasing the incident intensity to the sample 104 does not much contribute to contrast improvement. FIG. 6B illustrates the Rayleigh limit. Intensity distributions at two points intersect with each other at peak intensity of 37%. Thus, when the upper limit value in the conditional expression is equal to or smaller than 1/0.37=2.7, two points with the Rayleigh limit or less can be clearly resolved.

Modification of First Embodiment

Figure 4B:
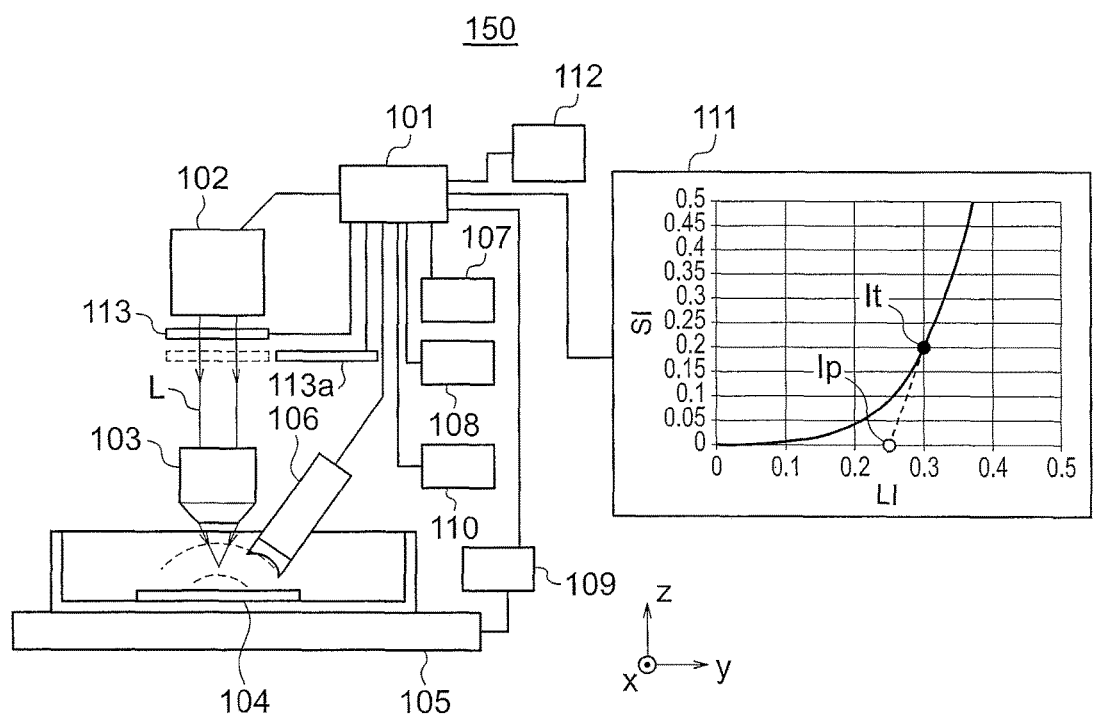
FIG. 4B is a diagram illustrating a schematic configuration of a photoacoustic microscope according to a modification of the first embodiment.

Next, a photoacoustic microscope 150 according to a modification of the first embodiment is described with reference to FIG. 4B. In the photoacoustic microscope 100 in the first embodiment, a threshold IP is automatically calculated on the basis of a predetermined flowchart, and after that, a super-resolved image is acquired.

In contrast, in the present modification, a super-resolved image is manually acquired. A photoacoustic microscope 150 in the present modification includes a display unit 111. The display unit 111 displays information representing intensity LI obtained by changing power per pulse output from a light source by a variable ND filter 113 and intensity SI of an acoustic signal. The information to be displayed is acquired from Step S101 to Step S109 in the above-mentioned flowchart. A user (not shown) acquires a threshold IP on the basis of the displayed information.

The amount of light is adjusted by the variable ND filter 113 such that the acquired threshold IP is set. In this manner, a super-resolved image can be manually obtained.

Second Embodiment

Figure 7A:
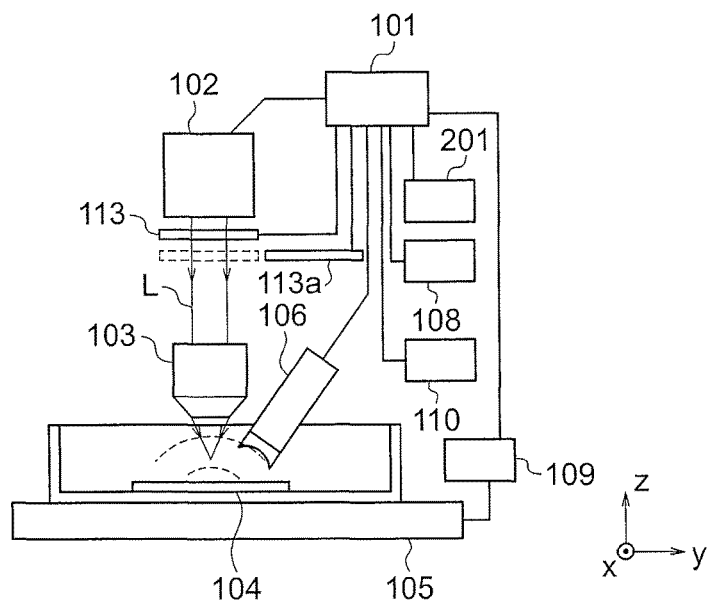
FIG. 7A is a diagram illustrating a schematic configuration of a photoacoustic microscope according to a second embodiment.

A photoacoustic microscope 200 according to a second embodiment is now described. FIG. 7A illustrates a schematic configuration of a photoacoustic microscope 200 according to the second embodiment. The photoacoustic microscope 200 in the second embodiment is configured to automatically measure a sample. The same parts as in the above-mentioned first embodiment are denoted by the same reference symbols to omit overlapping descriptions.

In the above-mentioned first embodiment, the threshold calculation unit 112 calculates, as the first step, a threshold IP for each sample 104 for every measurement of different samples 104. In contrast, in the second embodiment, the photoacoustic microscope includes an information storage unit 201 as an information unit. The information storage unit 201 stores therein information representing a relation between intensity obtained by changing power per pulse that is output from the pulse light source 102 and enters the sample 104 by the variable ND filter 113 and intensity of an acoustic signal generated from the sample 104.

For example, the information storage unit 201 has a table representing a relation between the stored information and the type of the sample 104. A user inputs the type of a sample to be observed via an input unit 108, which is a user interface such as a keyboard. In the information storage unit 201, necessary information or necessary information measured by a different device in advance can be stored at the factory shipment of the photoacoustic microscope.

The threshold calculation unit 112 calculates a threshold IP on the basis of the information stored in the information storage unit 201. For the calculation of the threshold IP, the control unit 101 adjusts the intensity LI obtained by changing power per pulse output from the light source by the variable ND filter 113. In this manner, a super-resolved image can be obtained.

The information storage unit 201 may store therein a threshold IP in addition to the information.

Modification of Second Embodiment

Figure 7B:
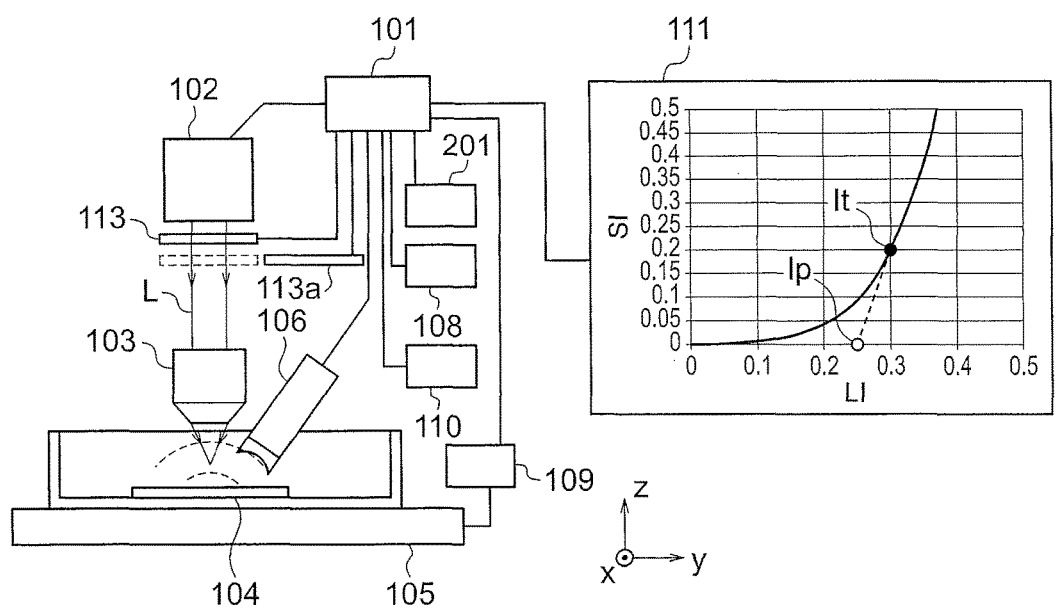
FIG. 7B is a diagram illustrating a schematic configuration of a photoacoustic microscope according to a modification of the second embodiment.

Next, a photoacoustic microscope 250 according to a modification of the second embodiment is described with reference to FIG. 7B. In the photoacoustic microscope 200 in the second embodiment, a threshold IP is calculated on the basis of information stored in the information storage unit 201 and on the basis of a predetermined flowchart, and after that, a super-resolved image is acquired.

In contrast, in the present modification, a super-resolved image is manually acquired. A photoacoustic microscope 250 in the present modification includes a display unit 111. The display unit 111 displays information representing intensity LI obtained by changing power per pulse output from a light source by a variable ND filter 113 and intensity SI of an acoustic signal. The information to be displayed is stored in the information storage unit 201. A user (not shown) acquires a threshold IP on the basis of the displayed information.

The amount of light is adjusted by the variable ND filter 113 such that the acquired threshold IP is set. In this manner, a super-resolved image is manually obtained.

Third Embodiment

Figure 8A:
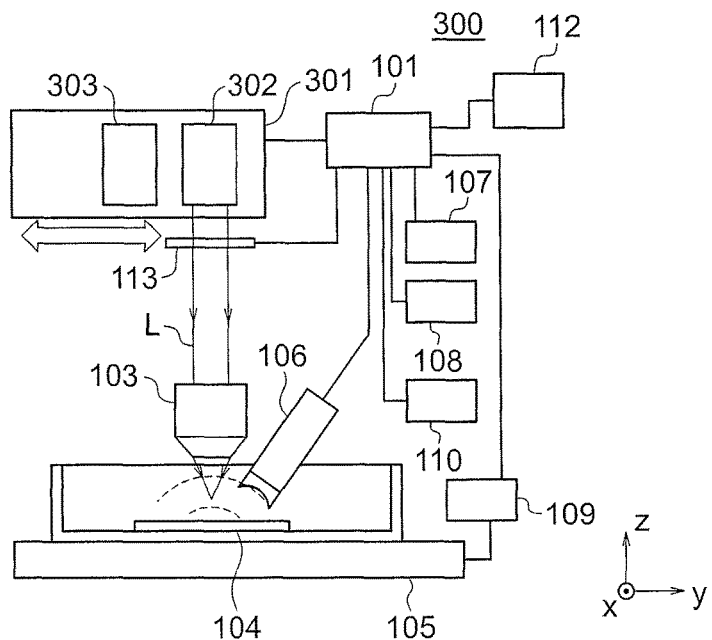
FIG. 8A is a diagram illustrating a schematic configuration of a photoacoustic microscope according to a third embodiment.

Next, a photoacoustic microscope according to a third embodiment of the present invention is described. FIG. 8A illustrates a schematic configuration of a photoacoustic microscope 300 in the third embodiment. The photoacoustic microscope 300 in the third embodiment is configured to automatically measure a sample. The same parts as in the above-mentioned first embodiment are denoted by the same reference symbols to omit overlapping descriptions.

As described above in the first embodiment and the second embodiment, in the case where the intensity LI obtained by changing power per pulse output from the light source by the variable ND filter and the intensity SI of the acoustic signal do not have a curvilinear relation, that is, have a linear relation, the threshold IP is present in a region smaller than the minimum adjustment unit of the variable ND filter 113.

As a solution, in the above-mentioned first and second embodiments, for example, the additional ND filter 113a configured to adjust the amount of light to ⅒ is inserted in the optical path. In this manner, the threshold IP present in a region smaller than the minimum adjustment unit of the variable ND filter 113 is calculated.

In contrast, the third embodiment differs from the first and second embodiments in that, for example, two different light sources 302 and 303 are alternatively used instead of using the additional ND filter 113a.

The photoacoustic microscope 300 in the third embodiment includes a pulse width changing unit 301. The pulse width changing unit 301 changes a pulse width of pulse light from the light source. For example, the pulse width changing unit 301 alternatively selects two different light sources 302 and 303. The light source 302 emits pulse light having an intensity distribution 302a illustrated in FIG. 8C. The light source 303 emits pulse light having an intensity distribution 303a illustrated in FIG. 8C The pulse width changing unit 301 selects the light source 302 or 303 so as to increase the pulse width of the pulse light in accordance with the information included in the information generation unit 107 (information unit) and representing the relation between the intensity per pulse output from the light source and the intensity of the acoustic signal generated from the sample 104. In this manner, a threshold IP can be obtained. As a result, a super-resolved image is obtained.

It is desired that the pulse width changing unit 301 increase the pulse width of the pulse light when the threshold IP is smaller than a predetermined value. When the threshold IP is close to zero, the width of pulse light entering the sample 104 can be increased to enable the threshold IP to be obtained more easily. As a result, a super-resolved image is obtained.

Modification of Third Embodiment

Figure 8B:
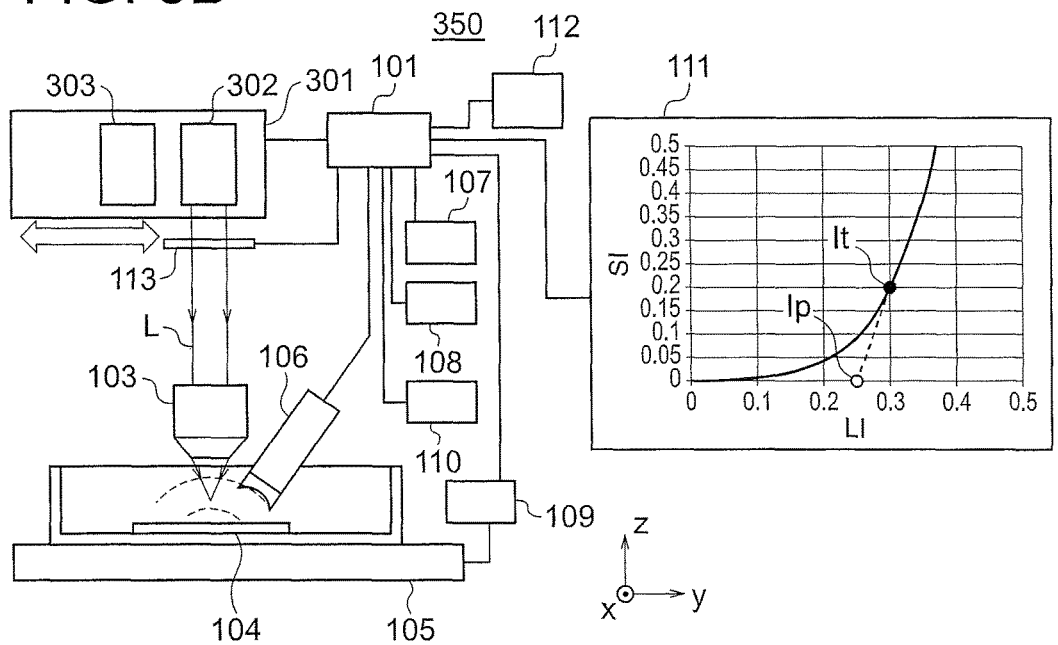
FIG. 8B is a diagram illustrating a schematic configuration of a photoacoustic microscope according to a modification of the third embodiment.
Figure 8C:
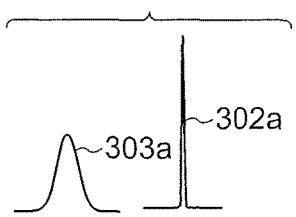
FIG. 8C is a diagram illustrating characteristics of pulse light output from a light source.

Next, a photoacoustic microscope 350 according to a modification of the third embodiment is described with reference to FIG. 8B. In the photoacoustic microscope 300 in the third embodiment, a threshold IP is automatically calculated on the basis of a predetermined flowchart, and after that, a super-resolved image is acquired.

In contrast, in the present modification, a super-resolved image is manually acquired. A photoacoustic microscope 350 in the present modification includes a display unit 111. The display unit 111 displays information representing intensity LI per pulse output from a light source and intensity SI of an acoustic signal. The information to be displayed is acquired from Step S101 to Step S109 in the above-mentioned flowchart. A user (not shown) acquires a threshold IP on the basis of the displayed information.

The photoacoustic microscope 350 selects the pulse light intensity distribution 302a or 303a such that the acquired threshold IP is set. In this manner, a super-resolved image can be manually obtained.

In the third embodiment and the modification thereof, instead of acquiring the information representing the relation between the intensity LI per pulse output from the light source and the intensity SI of the acoustic signal in accordance with the flowchart, the photoacoustic microscope may include an information storage unit that stores therein the information in advance.

Fourth Embodiment

Figure 9A:
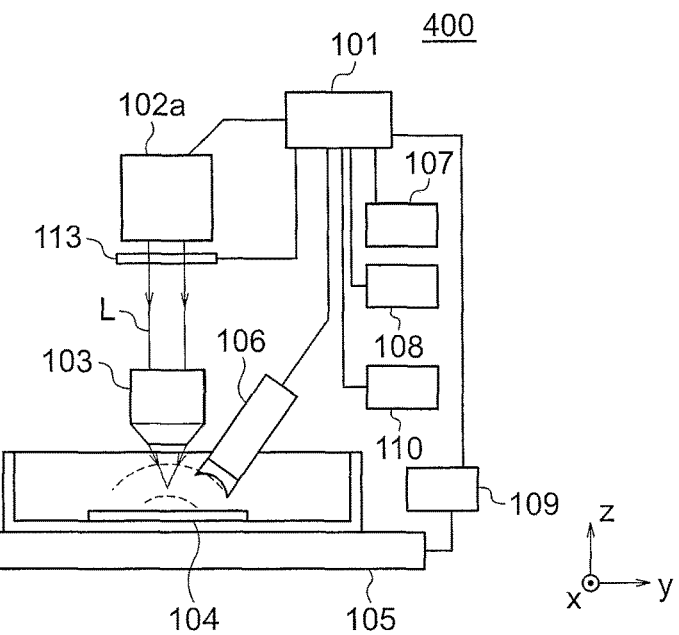
FIG. 9A is a diagram illustrating a schematic configuration of a photoacoustic microscope according to a fourth embodiment.

Next, a photoacoustic microscope according to a fourth embodiment of the present invention is described. FIG. 9A illustrates a schematic configuration of a photoacoustic microscope 400 in the fourth embodiment. The photoacoustic microscope 400 in the fourth embodiment is configured to automatically measure a sample. The same parts as in the above-mentioned first embodiment are denoted by the same reference symbols to omit overlapping descriptions.

As described above in the first embodiment and the second embodiment, when the intensity LI obtained by changing power per pulse output from the light source by the variable ND filter and the intensity SI of the acoustic signal do not have a curvilinear relation, that is, have a linear relation, a threshold IP is present in a region smaller than the minimum adjustment unit of the variable ND filter 113.

As a solution, in the above-mentioned first and second embodiments, for example, the additional ND filter 113a configured to adjust the amount of light to 1/10 is inserted in the optical path. In this manner, the threshold IP present in a region smaller than the minimum adjustment unit of the variable ND filter 113 is calculated.

In contrast, in the fourth embodiment, the photoacoustic microscope includes a CW light source 102a configured to continuously emit light instead of using the additional ND filter 113a. The control unit 101 controls pulses of voltage and current for driving the CW light source 102a. In this manner, pulse light 402a and pulse light 402b illustrated in FIG. 9C can be output.

The control unit 101 controls pulses of voltage and current for driving the CW light source 102a so as to increase the pulse width of the pulse light in accordance with the information included in the information generation unit 107 (information unit) and representing the relation between the intensity per pulse output from the light source and the intensity of the acoustic signal generated from the sample 104. In this manner, a threshold IP can be obtained. As a result, a super-resolved image is obtained.

For example, the pulse width of the pulse light is increased when the threshold is smaller than a predetermined value.

It is desired that the pulse width of the pulse light from the CW light source 102a satisfy the following Conditional Expression (2):

$$50 \text{ ns} < PW < 500 \text{ ns} \qquad (2)$$

where PW is the pulse width of the pulse light from the light source.

In this manner, a threshold IP can be efficiently obtained. As a result, a super-resolved image is obtained.

Modification of Fourth Embodiment

Figure 9B:
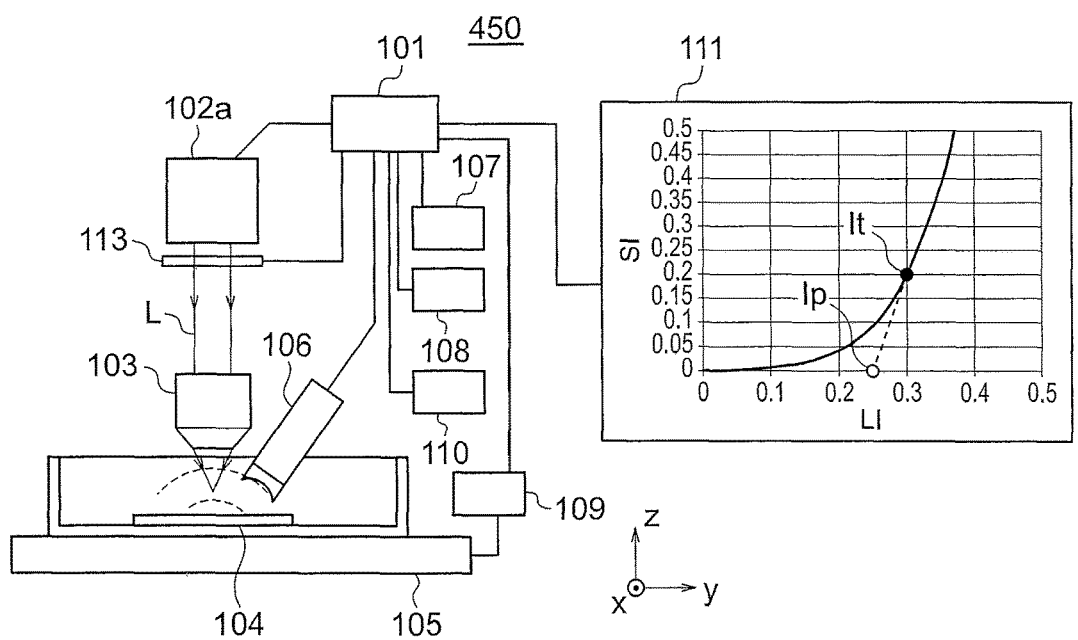
FIG. 9B is a diagram illustrating a schematic configuration of a photoacoustic microscope according to a modification of the fourth embodiment.
Figure 9C:
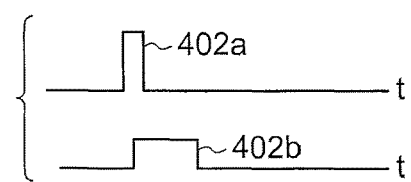
FIG. 9C is a diagram illustrating characteristics of pulse light output from a light source.

Next, a photoacoustic microscope 450 according to a modification of the fourth embodiment is described with reference to FIG. 9B. In the photoacoustic microscope 400 in the fourth embodiment, a threshold IP is automatically calculated on the basis of a predetermined flowchart, and after that, a super-resolved image is acquired.

In contrast, in the present modification, a super-resolved image is manually acquired. The photoacoustic microscope 450 in the present modification includes a display unit 111. The display unit 111 displays information representing a relation between intensity LI per pulse output from a light source and intensity SI of an acoustic signal. The information to be displayed is obtained from Step S101 to Step S109 in the above-mentioned flowchart. A user (not shown) acquires a threshold IP on the basis of the displayed information.

The photoacoustic microscope 450 controls voltage and current pulses for driving a CW light source 102a such that the acquired threshold IP is set. In this manner, a super-resolved image can be manually acquired.

In the fourth embodiment and the modification thereof, instead of acquiring the information representing the relation between the intensity LI per pulse output from the light source and the intensity SI of the acoustic signal on the basis of the flowchart, the photoacoustic microscope may include an information storage unit configured to store the information therein in advance.

As described above, the present invention can be variously modified within the scope not departing from the gist of the invention.

As described above, the present invention is effective to a photoacoustic microscope and a photoacoustic signal detection method capable of obtaining a super-resolved image by single photographing without damaging an object to be observed.

The present invention exhibits effects that a photoacoustic microscope and a photoacoustic signal detection method capable of acquiring a super-resolved image by single photographing without damaging an object to be observed can be provided.

What is claimed is:

1. A photoacoustic microscope, comprising:
a light source which generates pulse light;
a focusing optical system which focuses the pulse light emitted from the light source and irradiates a sample with the focused pulse light;
a photoacoustic signal detection sensor which detects an acoustic signal generated from the sample through irradiation of the pulse light; and
a controller configured to:
form an image signal of the sample based on the acoustic signal;
one of generate or store information representing a relation between intensity of the pulse light entering the sample and intensity of the acoustic signal generated from the sample;
change intensity of the pulse light from the light source based on the information;
calculate, based on the information, as a threshold, pulse light intensity with which the intensity of the acoustic signal relative to the intensity of the pulse light starts to increase;
change, based on the calculated threshold, the intensity of the pulse light from the light source to be equal to or more than the threshold; and
change the intensity of the pulse light from the light source such that the following Conditional Expression (1) is satisfied:

$$1.05 < IP/IT < 2.7 \quad (1)$$

where IT is the calculated threshold and IP is a peak value of intensity at a focus position of the pulse light after the change.

2. The photoacoustic microscope according to claim 1, further comprising a display which displays the information.

3. The photoacoustic microscope according to claim 1, wherein a pulse width of the pulse light from the light source satisfies the following Conditional Expression (2):

$$50 \text{ ns} < PW < 500 \text{ ns} \quad (2)$$

where PW is the pulse width of the pulse light from the light source.

4. The photoacoustic microscope according to claim 1, wherein the controller is further configured to change a pulse width of the pulse light from the light source.

5. The photoacoustic microscope according to claim 4, wherein the controller is configured to increase the pulse width of the pulse light in accordance with the information and represent the relation between the intensity of the pulse light entering the sample and the intensity of the acoustic signal generated from the sample.

6. The photoacoustic microscope according to claim 4 wherein the controller is configured to increase the pulse width of the pulse light when the threshold is smaller than a predetermined value.

7. The photoacoustic microscope according to claim 1, further comprising a scanner which two-dimensionally or three-dimensionally moves a position thereof relative to the pulse light and the sample.

8. A photoacoustic signal detection method, comprising:
emitting pulse light;
focusing the emitted pulse light and irradiating a sample with the focused pulse light;
detecting an acoustic signal generated from the sample through irradiation of the pulse light;
forming an image signal of the sample based on the acoustic signal;
one of generating or storing an information representing a relation between intensity of the pulse light entering the sample and intensity of the acoustic signal generated from the sample; and
changing intensity of the pulse light from a light source based on the information;
wherein the information generation comprises a threshold calculation, based on the information, as a threshold, pulse light intensity with which the intensity of the acoustic signal relative to the intensity of the pulse light starts to increase;
the method further comprising changing, based on the threshold calculated at the threshold calculation, the intensity of the pulse light generated at the emitting to be equal to or more than the threshold; and
wherein the pulse light intensity changing comprises changing the intensity of the pulse light generated at the emitting such that the following Conditional Expression (1) is satisfied:

$$1.05 < IP/IT < 2.7 \quad (1)$$

where IT is the threshold calculated at the threshold calculation, and IP is a peak value of intensity at a focus position of the pulse light after the change.

9. The photoacoustic signal detection method according to claim 8, further comprising:
displaying the information.

10. The photoacoustic signal detection method according to claim 9, wherein a pulse width of the emitted pulse light satisfies the following Conditional Expression (2):

$$50 \text{ ns} < PW < 500 \text{ ns} \quad (2)$$

where PW is a pulse width of the emitted pulse light.

11. The photoacoustic signal detection method according to claim 9, further comprising:
changing a pulse width of the emitted pulse light.

12. The photoacoustic signal detection method according to claim 11, wherein changing the pulse width comprises increasing the pulse width of the pulse light in accordance with the generated or stored information, the information representing the relation between the intensity of the pulse light entering the sample and the intensity of the acoustic signal generated from the sample.

13. The photoacoustic signal detection method according to claim 11 further comprising:
changing the pulse width, based on the calculated threshold,
wherein the pulse width changing comprises increasing the pulse width of the pulse light when the threshold is smaller than a predetermined value.

14. The photoacoustic signal detection method according to claim 9, further comprising:
moving relative positions of the pulse light and the sample two-dimensionally or three-dimensionally by scan.

* * * * *